United States Patent [19]

Holtman

[11] Patent Number: 4,544,596
[45] Date of Patent: Oct. 1, 1985

[54] STABILIZED ABSORBENT STRUCTURE CONTAINING NON-DELIGNIFIED WOOD PULP FIBERS

[75] Inventor: Dennis C. Holtman, Flemington, N.J.

[73] Assignee: Personal Products Company, Milltown, N.J.

[21] Appl. No.: 601,756

[22] Filed: Apr. 18, 1984

[51] Int. Cl.[4] .......................... D21F 7/00; D21H 3/00
[52] U.S. Cl. ..................... 428/171; 428/296;
428/198; 428/288; 604/374; 162/50; 162/192;
264/23; 156/73.1
[58] Field of Search ............................... 604/374–376;
428/171, 296, 198; 162/50, 192; 264/23;
156/73.1

[56] References Cited

U.S. PATENT DOCUMENTS

| 4,000,032 | 12/1976 | Bergstrom et al. | 162/50 X |
| 4,047,531 | 9/1977 | Karami | 604/374 |
| 4,135,024 | 1/1979 | Callahan et al. | 428/171 |
| 4,154,883 | 5/1979 | Elias | 428/171 |
| 4,215,692 | 8/1980 | Levesque | 604/374 |
| 4,226,237 | 10/1980 | Levesque | 604/374 |
| 4,287,140 | 9/1981 | Peters et al. | 264/23 |
| 4,391,672 | 7/1983 | Lehtinen | 162/192 |

Primary Examiner—George F. Lesmes
Assistant Examiner—Nancy A. B. Swisher
Attorney, Agent, or Firm—Martha A. Michaels

[57] ABSTRACT

A batt of non-delignified fibers is stabilized by applying ultrasonic energy thereto in narrow compressed lines which aid in distributing liquid within the batt. The fibers are partially delignified at fiber intersections which are hydrogen bonded. Supplementary stabilization may be provided by thermoplastic bond sites.

16 Claims, 6 Drawing Figures

STABILIZED ABSORBENT STRUCTURE CONTAINING NON-DELIGNIFIED WOOD PULP FIBERS

TECHNICAL FIELD

This invention relates to an absorbent structure for use in diapers, sanitary napkins, and the like. More particularly, the invention relates to an improved absorbent structure including non-delignified wood pulp fibers.

BACKGROUND OF THE INVENTION

For many years it has been well known to employ natural wood pulp fibers in the manufacture of the absorbent pad or core of disposable products such as diapers, sanitary napkins, surgical dressings, and the like. In the most general sense, there are but two basic processes, chemical and mechanical, for producing pulp fibers from natural wood. The characteristics of the pulp produced by the two basic processes differ considerably and, depending upon the intended final use to be made thereof, each has certain advantages and disadvantages.

In chemical wood pulping, there is a total or partial digestion and removal of the hydrophobic constituents of the wood, such as, lignin, carbohydrates and other nonligneous materials. The yield of chemical pulp is predictably low and expensive, on the order of around 50%.

Mechanical pulping processes are more cost efficient, producing yields on the order of 90% and higher. Understandably, mechanical wood pulp, sometimes known is refiner pulp, is substantially hydrophobic due to the presence of lignin and other non-absorbing materials.

More recently, there has been increasing use of wood pulp produced by thermo-mechanical processes. Thermo-mechanical pulp (TMP) is essentially mechanical pulp, but has modified qualities because of an additional heating step. The thermomechanical process involves a step of first heating the wood chips to about 270° F., usually with steam, to soften them for further mechanical processing. This heating stage tends to soften but not remove the lignin but also to loosen the individual wood fibers to ease actual defibration. Thermo-mechanical pulp thus has somewhat longer fibers than plain refiner pulp and produces structures of higher loft and greater flexibility.

Non-delignified wood pulp fibers, such as the thermo-mechanically produced wood pulp fibers, refiner produced wood pulp fibers, or the like, have become quite important in the last few years. These wood pulp fibers, also referred to as "high yield" wood pulp fibers, have become increasingly important for several reasons. The processes used to produce the fibers not only utilize more of the raw material than typical chemical processes, but the non-delignified wood pulp processes also reduce the environmental problems caused by chemical processing. Specifically, the "high yield" processes cause considerably less air pollution and water pollution than do the counterpart chemical processes. These various factors and the concomitant economic considerations make the high yield processes, such as the thermomechanical pulp process, very attractive.

Non-delignified wood pulp processes have been known for some time and are usually developed primarily for paper grade wood pulps, newsprint, and the like. These wood pulps have not been well accepted in absorbent type products, such as sanitary napkins, disposable diapers, and the like, primarily because of their relatively poor performance as the absorbent core for such products.

Conventional chemically processed wood pulp fibers have a degree of cohesive strength when placed in an air-laid web structure. Typically chemically processed wood pulp fibers are somewhat collapsed and appear in ribbon-like form. This form permits fiber entanglement during the air-laid web processing and hence results in a web having a degree of cohesiveness and fibrous web integrity.

In contrast, the non-delignified wood pulp fibers are non-collapsed, stiffer and more resilient. Webs formed of these fibers, although possessing a greater potential liquid holding capacity, have poor integrity and hence tend to break apart.

Furthermore, absorbent structures made from non-delignified wood pulp fibers are substantially hydrophobic and not readily wettable. For any absorbent structure to be satisfactory, it is highly desirable for the structure to (1) readily accept liquid, (2) easily transport the liquid from one portion of the structure to another, and (3) hold the liquid accepted.

Various techniques have been developed or suggested for improving the absorbent characteristics of non-delignified wood pulp, such as removing the fines from the wood pulp product or providing various solvent or other chemical treatments to the wood pulp product to both bleach the pulp and improve its absorbency. However, these techniques increase the economics or cost of the wood pulp and, in some instances, increase the pollution problem and, hence, do not take full advantage of the non-delignified wood pulp process.

Development of the use of mechanical wood pulp and thermo-mechanical pulp and some of the problems encountered in such use may best be appreciated by reference to some illustrative prior art examples. In "Mechanical Pulp In Absorbent Qualities", published by The Norwegian Pulp and Paper Institute (September, 1973) E. Bohmer et al describe the possible use of plain refiner or thermo-mechanical pulp in place of chemical pulp on a basis of cost, but conclude that it cannot achieve the liquid-holding capacity of chemical pulp. In "Thermo-Mechanical Pulp For Diapers, Other Absorbent Products" (November 1975) Weyerhaeuser Company describes its new thermo-mechanical process for making pulp called Eco-Fluff and some of its potential uses. Among U.S. Patents: U.S. Pat. No. 4,047,531 teaches a two-layer pad, one of mechanical or thermo-mechanical pulp and the second of thermo-mechanical or chemical pulp; U.S. Pat. No. 4,120,747 teaches an absorbent paper made of thermo-mechanical or chemi-thermo-mechanical pulp; and U.S. Pat. No. 4,215,692 teaches an absorbent structure comprising a mixture of mechanical wood pulp (thermo-mechanical or refiner) and peat.

Other techniques for developing absorbent products utilizing non-delignified wood pulps have been suggested. One technique is disclosed in British Pat. No. 1,500,053 and uses fibers of specific measurement; that is, length and diameter. The surface hydrophilicity of the fibers is increased by bleaching and the hydrophilic fibers are air-laid in web form and compressed to a specific density. Bleaching followed by compression substantially increases the wettability of the otherwise hydrophobic structure, but at the same time, reduces the liquid holding capacity of an absorbent structure made from non-delignified wood pulp fibers.

As mentioned above, for any absorbent structure to be satisfactory, it is not only necessary for the structure to hold liquid but also tb readily accept liquid and transport it. The liquid holding capacity of the absorbent structure relates to the pore size of the fibrous bed and the wet bending modulus of the fibers. If the pore size (i.e., the spaces surrounding the fibers) is large and the wet bending modulus (i.e., stiffness) of the fibers is high, then the structure will have a relatively high liquid holding capacity but generally does not transport (wick) liquid readily. On the other hand, if the pore size is smaller and the bending modulus relatively low, the structure readily wicks liquid but will have a lower liquid holding capacity.

The fibers from the non-delignified wood pulp process can provide an absorbent structure having a large pore size and a high wet bending modulus of the fibers, however, such absorbent structures do not readily accept liquid, nor will the structure be readily densified or embossed to promote wicking.

As indicated by the cited illustrative references, the numerous efforts in this highly developed art to provide an absorptive structure utilizing cost efficient and desirable thermo-mechanical pulp are beset with difficulties that remain unsolved. These difficulties are partially or completely overcome by the present invention.

SUMMARY OF THE INVENTION

In accordance with one aspect of the present invention, a single layer absorbent batt is provided that is formed of non-delignified wood pulp fibers, such as thermo-mechanical wood pulp fibers. Improved stability is imparted to the batt by applying ultrasonic energy thereto in spaced, narrow compressed lines. The application of ultrasonic energy causes delignification in at least some fibers in the spaced, narrow compressed lines and hydrogen bonding of fiber intersections where there is no lignin. The thus formed hydrogen bonds within the narrow compressed lines add strength and stability to the batt, and the lines themselves provide a wicking mechanism for directing liquid away from a wetted area.

In accordance with another aspect of the present invention, thermoplastic bond sites are provided at the narrow compressed lines of a batt of the type described in the preceding paragraph to add further stability to the batt. The thermoplastic bond sites may be provided by distributing a thermoplastic material, such as fibers or a powder, throughout the batt; or by adhering a thermoplastic scrim material, or other thermoplastic fiber layer, to the narrow compressed lines during the application of ultrasonic energy.

In accordance with still another aspect of the present invention, a layer of chemical pulp is adhered to the narrow compressed lines of a batt layer of the type described above by thermoplastic bond sites that are formed during the application of ultrasonic energy. This may be accomplished by interposing a thermoplastic bonding layer between the layers of non-delignified wood pulp fibers and chemical wood pulp fibers prior to the application of ultrasonic energy. A batt of the type described immediately above, also preferably, has an integral wicking layer on the outer surface of the chemical wood pulp fiber layer, for improved batt stability and liquid transport.

DESCRIPTION OF THE PREFERRED EMBODIMENTS

Figure 1:
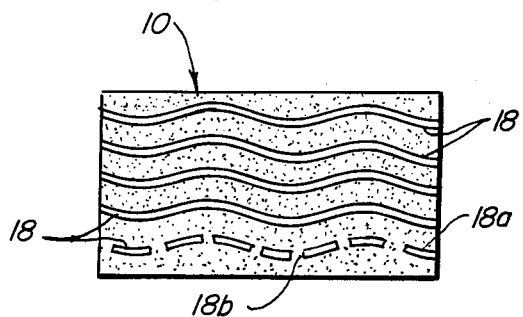
FIG. 1 is a plan view of an absorbent batt formed in accordance with the present invention.

While this invention is susceptible of embodiment in many different forms, there is shown in the drawings and will herein be described in detail preferred embodiments, with the understanding that the present disclosure is to be considered as an exemplification of the principles of the invention and is not intended to limit the invention to the embodiments illustrated. The scope of the invention will be pointed out in the appended claims.

Figure 2:
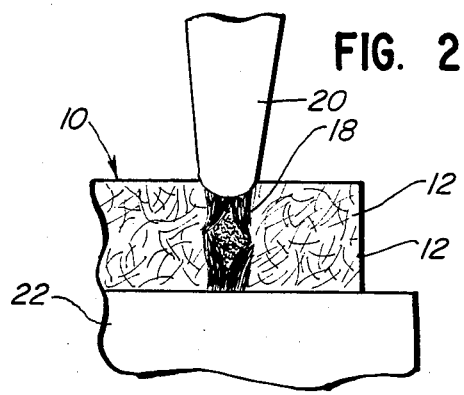
FIG. 2 is an enlarged schematic view illustrating the step of applying ultrasonic energy.
Figure 6:
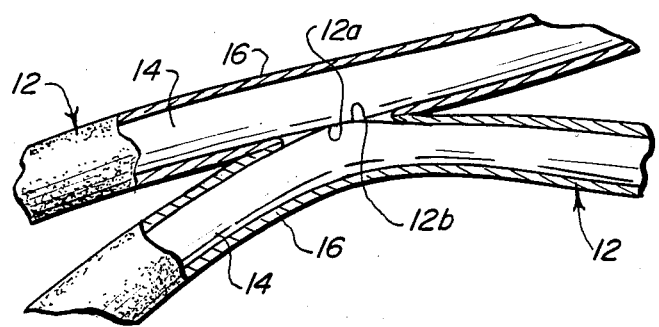
FIG. 6 is a greatly enlarged view of two non-delignified wood pulp fibers bonded in accordance with the present invention.

Referring now to FIGS. 1 and 2, a novel batt 10 is illustrated therein which is formed entirely of non-delignified wood pulp fibers 12, such as thermo-mechanical wood pulp fibers. As is well known in the art, non-delignified wood pulp fibers are of paper making fiber length, on the order of ¼ inch or less, and contain a cellulose core 14 which is substantially completely covered, or coated, with lignin 16 (FIG. 6). In accordance with the present invention, batt 10 is subjected to ultrasonic energy in preselected areas to cause adjacent fibers in such areas to adhere to one another by hydrogen bonding of contacting delignified fiber portions 12a and 12b. In the embodiment illustrated in FIG. 1, the ultrasonic energy is applied in spaced, parallel lines, or rows 18, which are sinuously shaped. Lines 18 can have a width dimension of 1/16 inch or less, but it is preferred that the lines have a width dimension of from about 1/16 inch to about ¼ inch. The spacing between the lines should be within the range of from about ¼ inch to about 2 inches.

One type of apparatus suitable for use in carrying out the present invention is illustrated schematically in FIG. 2, and such apparatus includes a horn 20 positioned in juxtaposed relationship with respect to an anvil 22, with batt 10 being interposed therebetween. Apparatus of this type is commercially available from Branson Instruments, Incorporated of Stamford, Conn. It will be understood that the horn 20 will have a batt engaging portion for each line 18, and that only one such batt engaging portion is shown in FIG. 2. It will also be understood that horn 20 and anvil 22 are movable relative to one another to compressively engage batt 10 therebetween.

When horn 20 is energized, it transmits vibrations in the ultrasonic frequency range to batt 10, and the heat induced by such vibrations causes the lignin in the non-delignified wood pulp fibers 12 to heat soften or melt. This delignification of the fibers 12 occurs primarily at fiber intersections, where it is thought that the induced ultrasonic vibrations cause the fibers to rub against one another, thereby causing localized delignification of the fibers at fiber intersections. The moisture content of the air under ambient atmospheric conditions is sufficient to permit hydrogen bonding of the hydroxyl molecules in the delignified areas 12a and 12b of fibers 12.

The application of ultrasonic energy as described above is substantially uniform throughout the cross-sectional thickness of the batt, and as a result, when there is relative longitudinal movement between batt 10 and horn 20 and anvil 22, compressed narrow lines 18 are produced wherein the non-delignified fibers 12 are hydrogen bonded to one another at fiber intersections. The resulting batt has markedly improved strength and stability, and the smaller capillaries in the lines 18 provide a wicking mechanism for directing liquid longitudinally of the batt. In a preferred embodiment of the invention, the density within lines 18 is 0.35 gm/cc, or higher, whereas the density of the batt 10 between lines 18 is about 0.05 gm/cc. However, densities in lines 18 in the range of 0.2 gm/cc to 0.8 gm/cc are acceptable. Sinuously shaped, or zig-zag, lines are preferred over straight lines for improved batt stability. The lines 18 need not be continuous and can be comprised of spaced bonded zones 18a separated by unbonded zones 18b, as is shown for the bottom line in FIG. 1. This latter configuration can be achieved by utilization of an anvil having a plurality of spaced land areas.

Figure 3:
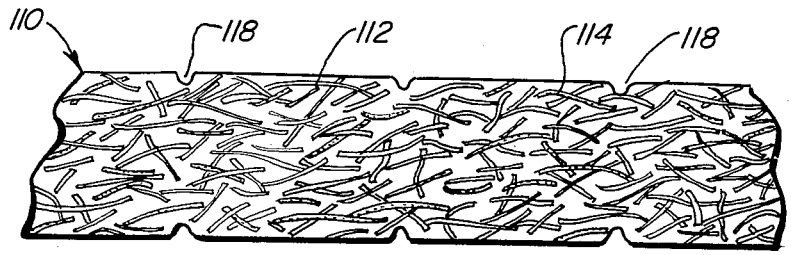
FIG. 3 is an enlarged cross-sectional view illustrating a second embodiment of the invention.

The stabilization of batt 10 can be further improved by incorporating a thermoplastic material in the batt. FIG. 3 is a diagrammatic representation of an enlarged cross-sectional view of an absorbent batt 110 embodying the principles of the invention. Batt 110 is formed of a substantially homogeneous mixture or blend of non-delignified wood pulp fibers 112 and thermoplastic fibers 114 (stippled) intermixed therewith. Both the non-delignified wood pulp fibers 112 and thermoplastic fibers 114 are of paper making fiber length, on the order of ¼ inch or less. The thermoplastic fibers 114 may consist of any of a number of low melt plastics such as polyethylene, polypropylene, low melt polyester, polyvinylchloride and polyvinylidene chloride, with polyethylene being the preferred plastic. In any case, the melting temperature of the thermoplastic fibers should be on the order of 30° to 40° F. below the melting point of lignin which, while not fixed, is approximately 275° F. An example of thermoplastic fibers of the present invention are synthetic wood pulp fibers formed of polyethylene that are sold by Crown Zellerbach under the trademark SWP.

Batt 110 comprises predominantly non-delignified wood pulp fibers 112, on the order of 75 percent to 95 percent of the blend. Concomitantly, the concentration of thermoplastic fibers 114 is in the range of 5 percent to 25 percent. Such a batt may be formed with a Dual Rotor Webber or with a Rando Webber of well known construction.

When ultrasonic energy is applied to batt 110 as set forth above, at least a substantial percentage of the short thermoplastic fibers are melted and the melted fibers form beads or globules that flow to the intersections of non-delignified fibers. Upon cooling and solidification, the globules define thermoplastic fiber bond sites which cooperate with the hydrogen bonds to retain the non-delignified fibers in a stabilized fiber network. With this arrangement, the interstices between the non-delignified fibers in lines 118 are maintained to thereby provide the batt with enhanced absorptive capacity. While it is contemplated that substantially all of the short thermoplastic fibers may be melted to form beads or globules, some of the thermoplastic fibers may retain at least a portion of their fiber identity, in which case such fibers may fuse to one another and to the non-delignified fibers to provide further thermoplastic fiber bond sites.

Figure 4:
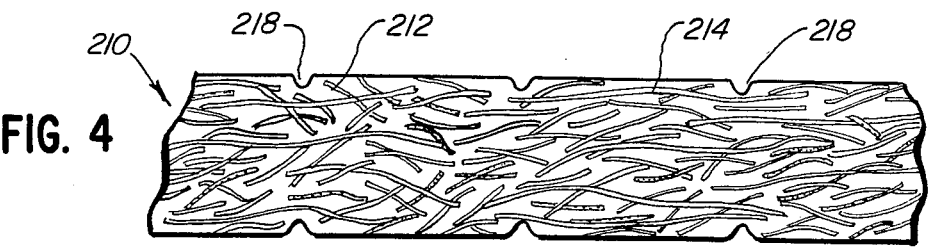
FIG. 4 is an enlarged cross-sectional view like FIG. 3, but showing another embodiment of the invention.

Referring now to FIG. 4, a further embodiment of the invention is illustrated wherein the batt 210 consists of a generally uniform blend of non-delignified wood pulp fibers 212 and thermoplastic fibers 214 that are of staple length, i.e., ½ to 3 inches. As with the embodiment of FIG. 3, batt 210 comprises predominantly non-delignified wood pulp fibers 212 in a range of from about 75 percent to about 95 percent of the blend, whereas the staple length thermoplastic fibers comprise about 5 percent to about 25 percent of the blend. Like batt 110, batt 210 may be formed with a Rando Webber.

When ultrasonic energy is applied to batt 210, the portions of the thermoplastic fibers 214 in lines 218 are heat softened, or melted, to provide thermoplastic bond sites in the lines 218 in addition to the hydrogen bonds between the non-delignified fibers. Since the staple length fibers 214 are drawn and more highly crystalline than the short thermoplastic fibers of the embodiment of FIG. 3, such fibers will maintain their fiber identity after the application of ultrasonic energy and will bond to one another and to the non-delignified fibers. It is preferred that the lines 218 be spaced sufficiently closely to one another, so that at least some of the staple length thermoplastic fibers will extend therebetween, and be bonded in, adjacent lines 218 to further enhance the stability of the batt 210.

While thermoplastic fibers have been illustrated in the embodiments of FIGS. 3 and 4, the present invention is not limited to the use of fibers to supplement the stabilization attributable to the hydrogen bonding in the embodiment of FIG. 1. For example, a thermoplastic powder (polyethylene, polyamide, etc.) could be incorporated into the batt instead of thermoplastic fibers 114 and 214. Likewise, the supplementary stabilization attributable to the thermoplastic material need not be provided by thermoplastic bond sites distributed throughout the cross-sectional thickness of the batt. For example, a thermoplastic fibrous layer or scrim could be bonded to the non-delignified fibers at the surface of the batt in the narrow compressed lines during the application of ultrasonic energy.

Figure 5:
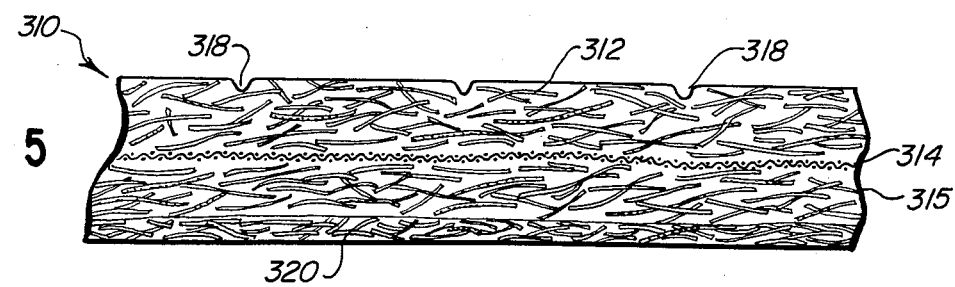
FIG. 5. is an enlarged cross-sectional view like FIGS. 3 and 4, and illustrating still another embodiment of the invention.

Referring now to the embodiment of FIG. 5, a multi-layer batt 310 is illustrated which includes as a first layer a web of non-delignified wood pulp fibers 312, a second layer in the form of a thermoplastic scrim 314 in surface-to-surface contact with the first layer, and a third layer of chemical wood pulp fibers 315. When ultrasonic energy is applied to batt 310 to form the narrow compressed lines 318, as described above, scrim 314 provides thermoplastic bond sites with the fibers of both the first and third layers to unify the batt. Thermoplastic powders, foams or films may be substituted for the scrim 314 to provide the bonding layer. In the embodiment of FIG. 5, the chemical wood pulp fibers at the outer surface of the third layer are preferably bonded to one another to form a paper-like densified skin 320 in accordance with the teachings of Burgeni U.S. Pat. No. 3,017,304.

The above detailed description of this invention has been given for clarity of understanding only. No unnecessary limitations are to be understood therefrom, as modifications will be obvious to those skilled in the art.

What is claimed:

1. An absorbent batt comprising: a web including an assemblage of non-delignified wood pulp fibers, said web having compressed narrow lines wherein said fibers in said lines are at least partially delignified at fiber intersections by ultrasonic energy treatment within said lines and said fiber intersections are hyrogen bonded to one another to stabilize said batt, said lines providing a fluid distribution network within said batt and having a width up to about ¼ inch and wherein the density in said lines is at least 0.2 gm/cc.

2. An absorbent batt as set forth in claim 1 wherein said non-delignified wood pulp fibers comprise thermomechanical wood pulp fibers.

3. An absorbent batt as set forth in claim 2 in which said lines have a width within the range of from about 1/16 inch to about ¼ inch, and wherein said lines are spaced from one another by a dimension within the range of from about ¼ inch to about 2 inches.

4. An absorbent batt as set forth in claim 1 wherein said lines are sinuously shaped.

5. An absorbent batt as set forth in claim 1 wherein thermoplastic bond sites are provided at said compressed narrow lines.

6. An absorbent batt as set forth in claim 5 wherein said thermoplastic bond sites are provided by globules of thermoplastic material at a plurality of fiber intersections within said compressed narrow lines.

7. An absorbent batt as set forth in claim 5 wherein said thermoplastic bond sites are provided by a thermoplastic scrim material fused to at least some of the non-delignified fibers within said narrow compressed lines.

8. An absorbent batt as set forth in claim 5 wherein said thermoplastic bond sites are provided by a layer of thermoplastic fibers fused to at least some of the non-delignified fibers within said narrow compressed lines.

9. An absorbent batt as set forth in claim 5 wherein said thermoplastic bond sites are provided by thermoplastic fibers uniformly blended within said web.

10. An absorbent batt as set forth in claim 9 wherein said thermoplastic fibers are staple length fibers, at least some of said staple length fibers extending between said narrow compressed lines.

11. An absorbent batt as set forth in claim 1 including a layer of chemical pulp bonded to said web.

12. An absorbent batt as set forth in claim 11 wherein said layer of chemical pulp is bonded to said narrow compressed lines by thermoplastic bond sites.

13. An absorbent batt as set forth in claim 12 wherein said layer of chemical pulp includes on an outer portion thereof a paper-like densified compacted cellulosic skin.

14. The method of forming an absorbent batt comprising: providing an assemblage of non-delignified woodpulp fibers; and applying ultrasonic energy to said assemblage of fibers in spaced, narrow lines to (1) at least partially delignify said fibers at fiber intersections within said spaced, narrow lines, and (2) hydrogen bond said fibers at said fiber intersections to stabilize said batt and provide a fluid distribution network within said batt.

15. The method of claim 14 wherein said ultrasonic energy is applied in spaced, narrow, sinuous lines in said fiber assemblage.

16. The method of claim 14 including the further step of incorporating a thermoplastic material into said assemblage of fibers prior to the step of applying ultrasonic energy, and wherein said step of applying ultrasonic energy is effective to at least partially melt said thermoplastic material and provide thermoplastic bond sites within the spaced, narrow lines of said batt.

* * * * *